United States Patent
Martello

(10) Patent No.: US 6,168,598 B1
(45) Date of Patent: Jan. 2, 2001

(54) SOFT TISSUE SECURING ANCHOR

(76) Inventor: Jeannette Martello, 713 Orange Grove Ave., South Pasadena, CA (US) 91030

(*) Notice: Under 35 U.S.C. 154(b), the term of this patent shall be extended for 0 days.

(21) Appl. No.: 09/089,231

(22) Filed: Jun. 2, 1998

Related U.S. Application Data

(60) Provisional application No. 60/048,284, filed on Jun. 2, 1997.

(51) Int. Cl.$^7$ .................................................. A61B 17/56
(52) U.S. Cl. ............................................. 606/74; 606/72
(58) Field of Search .................. 606/74, 72, 73, 606/75, 93, 94, 95, 59–65; D8/387; 52/410; 223/6; 411/531, 539, 156

(56) References Cited

U.S. PATENT DOCUMENTS

| | | | |
|---|---|---|---|
| 4,988,351 | * 1/1991 | Paulos et al. | 606/72 |
| 5,326,205 | 7/1994 | Anspach, Jr. et al. | 411/43 |
| 5,370,662 | 12/1994 | Stone et al. | |
| 5,443,482 | 8/1995 | Stone et al. | 606/232 |
| 5,505,735 | 4/1996 | Li | 606/72 |
| 5,626,612 | 5/1997 | Bartlett. | |
| 5,778,623 | * 7/1998 | Powell | 52/410 |

* cited by examiner

Primary Examiner—Michael Buiz
Assistant Examiner—Lien Ngo
(74) Attorney, Agent, or Firm—Terry M. Gernstein

(57) ABSTRACT

A surgical anchor is provided with one or more anchor holes distributed around the head of the anchor. Each anchor hole is inclined to allow attachment of one or more sutures to the anchor either before, during or after the anchor is seated in a bone. The upper and lower apertures of each anchor hole are chamfered, and the chamfered areas from the anchor hole to the outside edge shall be polished or somehow smoothed to remove sharp edges and rough areas which may cause friction and abrasion to soft tissue or suture material. The lower surface of the anchor head may be angled to further simplify the task of feeding a surgical needle through the anchor hole after the anchor is seated into bone.

76 Claims, 5 Drawing Sheets

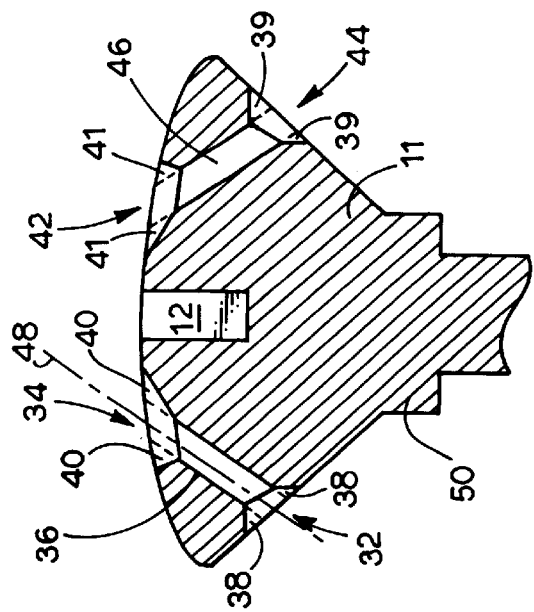
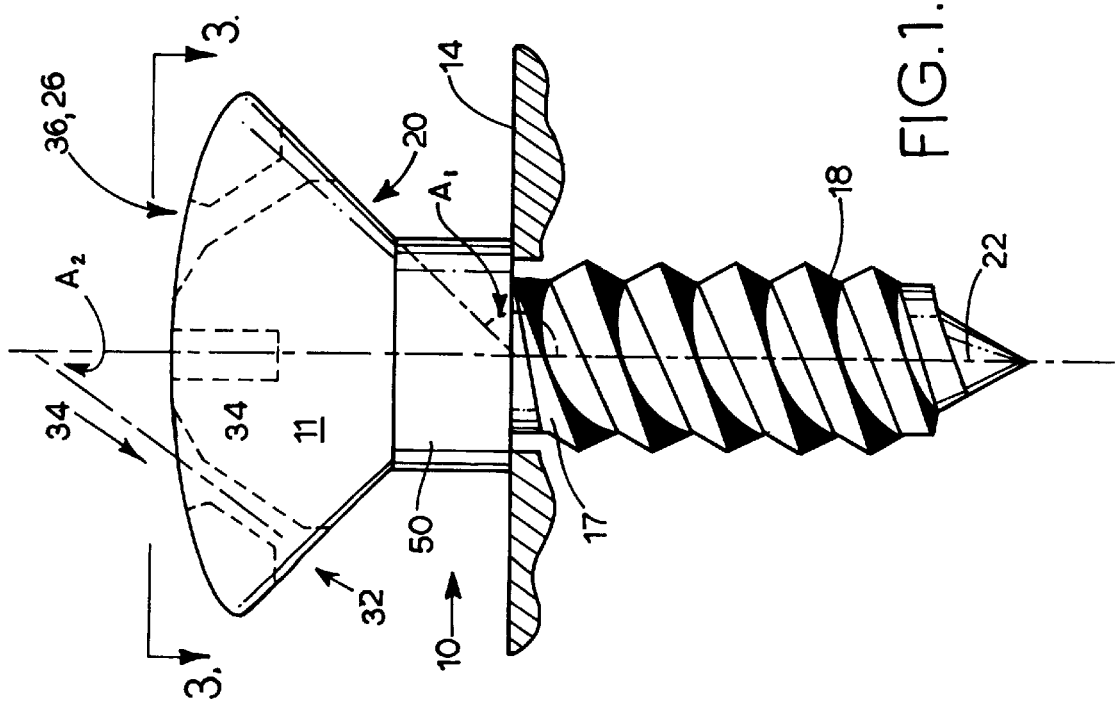

SOFT TISSUE SECURING ANCHOR

RELATED APPLICATIONS

This invention claims priority of copending U.S. provisional patent application Ser. No. 60/048,284 filed Jun. 2, 1997.

BACKGROUND OF THE INVENTION

1. Field of the Invention

The present invention relates generally to the field of surgical devices. In particular, this invention relates to anchors for attaching soft tissue to bone, and or to other soft tissue.

2. Background of the Invention

There are a number of conventional devices currently being marketed as anchors for securing soft tissue to bone. These devices have found application in surgical repair procedures throughout the human body. The conventional devices have some disadvantages which render them less than optimal for use in many operative procedures.

Conventional devices are generally metal, plastic or absorbable anchors which are screwed or press fit into pre-drilled holes in a bone. The conventional anchors have a suture-securing hole transverse to the long axis of the anchor. The suture-securing hole is generally located in the shank of the anchor which is therefore at or near the surface of the bone when the anchor is properly seated in the bone. The orientation of the suture securing hole in conventional anchors typically requires that the anchor have the suture threaded through the suture-securing hole, before the anchor is secured to the bone. A surgeon has little or no choice of the angle or position of tissue approximation, that is of attachment, when using such conventional anchors. Once a conventional anchor is secured in place, a surgeon is generally not able to rethread a suture through the suture-securing hole if the suture should break or otherwise come loose. Usually, a new anchor kit needs to be opened if the suture breaks. This leads to the inefficient use of the patient's operative time as well as the surgeon's time. Conventional anchors also only accommodate one suture per anchor and surgeons have little or no choice of suture material to be used with a particular anchor since the anchor kits are pre-loaded or come with a specific suture type.

Such conventional anchors require a surgeon to follow many steps and use special tools to successfully load and use the conventional anchors. First, the surgeon must gather the special tools necessary to use the conventional anchor. Second, the surgeon must thread the suture provided with the conventional anchor using a specialized threading tool. Third, the surgeon must drill an anchor hole into the bone which will secure the conventional anchor. Fourth, the surgeon must attach a conventional anchor to a special insertion tool. Fifth, the surgeon must secure the conventional anchor into the hole prepared in step three. Sixth, the surgeon must apply an appropriate surgical needle to an end of the free suture. Seventh, the surgeon must approximate the soft tissue to the conventional anchor using the needle and suture.

SUMMARY OF THE INVENTION

In accordance with the present invention, a soft tissue securing anchor is provided with one or more anchor holes distributed around the perimeter of the head of the anchor in a variety of orientations.

A soft tissue securing anchor according to the present invention may be used to secure soft tissue to bone, or to reapproximate a plurality of soft tissue points to a single bone site or to approximate soft tissue to soft tissue. The materials from which a soft tissue securing anchor are fabricated may be the same as conventional anchors, i.e. an inert material. Specific materials that may be used include plastic, stainless steel, titanium alloys, or absorbable materials. Thus a soft tissue securing anchor according to the present invention has the same effect on a body in which it is surgically secured as conventional anchors. Additionally, all types of conventional absorbable or non-absorbable sutures may be used with the present invention.

In a first aspect of the present invention, the anchor holes are inclined so that with the soft tissue securing anchor seated in the bone, the upper and lower apertures of each anchor hole are accessible to attach separate sutures to each of the anchor holes using conventional surgical techniques, i.e. curved needles. Any other variety of surgical needles may also be used. Additionally, free sutures, without attached needles may be threaded through these holes. The inclined anchor holes allow a surgeon to efficiently attach soft tissue to the soft tissue securing anchor using her preferred surgical tools without the necessity of using a multiplicity of specialized tools. Thereby making any given surgery more efficient and cutting down on costly operative time as well as time that the patient is exposed to potentially life-threatening anesthesia. The presence of a plurality of anchor holes in a single soft tissue securing anchor permits a surgeon to secure a plurality of soft tissue points with fewer soft tissue securing anchors than she would have been required using conventional anchors that only accommodate a single suture.

In another aspect of the present invention, the lower surface of the anchor head is angled relative to the long axis of the soft tissue securing anchor. The angle chosen is dictated by the surgeon's choice of needle and suture for a particular application. The angle of the lower surface of the anchor head combined with the angle of the anchor holes allows the surgeon to efficiently attach one or more sutures to a single soft tissue securing anchor. This minimizes the amount of foreign bodies that are surgically placed in a patient's body. Foreign body tissue reaction may lead to an increased rate of infection and, therefore, with the present invention, the patient would benefit with a lowered rate of foreign body tissue reaction. Additionally, since the suture to anchor body interface is very important with respect to operative stability, the possibility of now securing multiple soft tissue points to one anchor via the present invention means that if a single suture were to break, the operative approximation of soft tissue to bone or soft tissue to soft tissue would not be lost, as it is with the breaking of a suture attached to a conventional anchor.

In a further aspect of the present invention, each aperture of each anchor hole is chamfered to accommodate surgical needles. The chamfered aperture simplifies the surgeon's task of introducing the surgical needle into the anchor hole by widening the entry and exit apertures, and thus funneling the surgical needle point to the center of the anchor hole. The chamfer also lessens the angle of approximation the surgeon must achieve with a surgical needle to successfully pass the surgical needle and suture through the anchor hole. The chamfered areas, from the anchor hole to the outside edge, shall be polished or somehow smoothed to remove sharp edges and rough areas which may cause friction and abrasion of the tissue-approximating suture or the soft tissue itself. The chamfered aperture also minimizes acute edges in contact with the suture to minimize abrading of the suture thus allowing the liberal use of sliding knots on sutures passing through the present invention.

In a still further aspect of the present invention, an anchor for securing soft tissue to bone or soft tissue to soft tissue includes a conventional attachment means having a long axis and a head at a first end of the long axis, a means to accommodate a securing or drive tool, and an anchor hole through the head, the anchor hole has an upper aperture and a lower aperture. The anchor hole is oriented to cause a line through the center of the anchor hole to intersect an extension of the long axis beyond the head.

In a still further aspect of the present invention, an anchor for securing soft tissue to bone or soft tissue to soft tissue includes an attachment means having a long axis and a head at a first end of the long axis, a means to accommodate a securing or drive tool, and an anchor hole through the head, the anchor hole having an upper aperture and a lower aperture, the anchor hole oriented to cause a line through the center of the anchor hole to be skew to the long axis.

In another still further aspect of the present invention, a surgical anchor for reapproximating soft tissue to bone or soft tissue to soft tissue includes a screw having a head, a shank and a threaded end, a shoulder between the body and the shank to provide a visual and tactile reference for proper head height above the bone, a means to accommodate a securing or drive tool, and a plurality of generally radial anchor holes disposed about the circumference of the head and extending through the head, each anchor hole describing an angle between 0 and 75 degrees from the shank to a line through the anchor hole.

These and other features and advantages of this invention will become further apparent from the detailed description and accompanying figures that follow. In the figures and description, numerals indicate the various features of the invention, like numerals referring to like features throughout both the drawings and the description.

BRIEF DESCRIPTION OF THE DRAWINGS

FIG. 1 is a side view of a soft tissue securing anchor according to the present invention.

FIG. 2 is a cross sectional view of the head of the soft tissue securing anchor of FIG. 1 along A–A'.

DETAILED DESCRIPTION OF THE PREFERRED EMBODIMENT(S)

Figure 3:
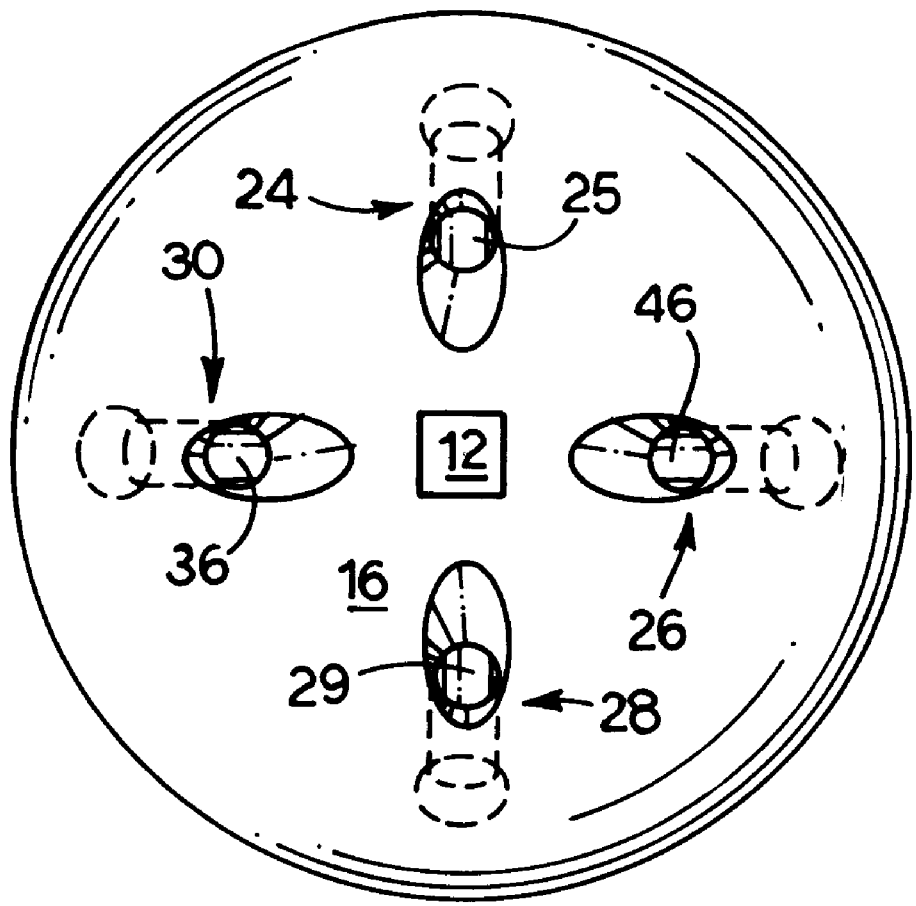
FIG. 3 is a top view of a soft tissue securing anchor according to the present invention.

Referring to FIG. 1, soft tissue securing anchor 10 includes head 11 and securing end 18. Securing end 18 may include any conventional means of securing a suture anchor into bone such as threads, barbs, fingers, toggle or molly bolts, and rivets. Suture anchor 10 may be secured into bone by any conventional means such as the application of torque or press-fit. The currently preferred embodiment of the present invention is a threaded, self tapping screw having a shoulder 50 which delineates head 11 from shank 17. Shoulder 50 provides a visual and physical indication to the surgeon to stop inserting soft tissue securing anchor 10 when shoulder 50 contacts bone 14. The size of shoulder 50 and the shape of head 11 are selected to permit access by surgical needle to both upper and lower apertures such as upper aperture 34 and lower aperture 32. Raising lower aperture 32 above bone 14 permits easy access to lower aperture 32. Head 11 may include a means for accommodating a drive tool such as a shaped head, tabs, flanges, channels, or one or more drive sockets such as drive socket 12 for securing anchor 10. A shaped head or drive socket such as drive socket 12 may be any conventional configuration compatible with surgical drive tools such as slotted, star, square, hex or alien shaped. Upper surface 16 of head 11 may be flat, convex or other conventional screw shape as shown in FIG. 2.

In accordance with one aspect of the present invention, lower surface 20 of head 11 may describe an angle $A_1$ between 90° and 150° from long axis 22. The angle of lower surface 20 may be determined by a surgeon's choice of needle and suture for a particular application. In the currently preferred embodiment of the present invention, the angle of lower surface 20 for a soft tissue securing anchor appropriate for cranial cosmetic surgery is about 40°–50° from long axis 22.

Referring now to both FIGS. 1 and 3, soft tissue securing anchor 10 includes anchor points 24, 26, 28 and 30. Each anchor point has an upper aperture and a lower aperture. Anchor hole 36 includes upper aperture 34 and lower aperture 32. Anchor holes 25, 29, 36 and 46 may be inclined at an angle $A_2$ (or $A_3$ of FIG. 5B) between 0° and 75° from long axis 22. The angle of inclination, the diameter of the anchor holes, and the shape of head 11 are selected to accommodate the surgical task and a surgeon's choice of needle. The object is to secure the anchor, leaving sufficient space between lower aperture 32 and bone 14 for the surgeon to easily secure a suture through the anchor holes such as anchor hole 36. In a preferred embodiment of the present invention, soft tissue securing anchor 10 is appropriate for cranial cosmetic surgery and anchor holes 25, 29, 36 and 46 are inclined in the range of about 35°–50° from long axis 22.

In a further aspect of the present invention, each aperture of each anchor hole is chamfered to accommodate surgical needles. Referring now to FIG. 2, anchor hole 36 connects upper aperture 34 and lower aperture 32. Chamfer 38 widens lower aperture 32, and chamfer 40 widens upper aperture 34. In a preferred embodiment of the present invention appropriate for cranial cosmetic surgery, the chamfers 38 and 40 of anchor hole 36 are about 45° from center line 48. The chamfers may be cut to a depth of 5% to 50% of the total length of an anchor hole. In a preferred embodiment of the present invention, chamfers 38, 40, 39 and 41 are cut to 25% of the total length of anchor holes 36 and 46 respectively. Chamfers 38 and 39 shall be polished or somehow smoothed, from anchor hole 36 and 46 respectively to lower surface 20 to remove sharp edges and rough areas which may cause friction and abrasion of soft tissue or suture material. Chamfers 40 and 41 shall be polished or somehow smoothed, from anchor hole 36 and 46 respectively to upper surface 16 to remove sharp edges and rough areas which may cause friction and abrasion of soft tissue or suture material.

A preferred embodiment of the present invention is shown in FIGS. 1 and 3. Soft tissue securing anchor 10 is a stainless steel, pan-head, self-tapping screw having four anchor points 24, 26, 28 and 30 equally spaced around head 11. The preferred technique for using a soft tissue securing anchor according to the present invention is for the surgeon to expose bone 14 which will secure soft tissue securing anchor 10 using conventional surgical techniques. A hole is drilled into bone 14 by conventional means using either a hand or power drill. Soft tissue securing anchor 10 is screwed into bone 14 by applying a torque to soft tissue securing anchor 10 using a conventional surgical drive tool inserted into drive socket 12. When shoulder 50 contacts bone 14 soft tissue securing anchor 10 is seated. The surgeon may remove the drive tool from soft tissue securing anchor 10 and reapproximate soft tissue to the area of bone 14 which secures soft tissue securing anchor 10 by using conventional surgical techniques and sewing suture to anchor points 24, 26, 28 and 30.

In alternative techniques, sutures may be secured to anchor points 24, 26, 28 and 30 before, during or after the process of seating soft tissue securing anchor 10 in bone 14. These techniques are suited to bone sites which limit access to head 11 after soft tissue securing anchor 10 is seated. Thus the suture may be secured to soft tissue securing anchor 10 before, during or after soft tissue securing anchor 10 is fully seated into bone 14. This allows the surgeon to adopt her technique to a variety of securing sites for soft tissue securing anchors.

Figure 4A:
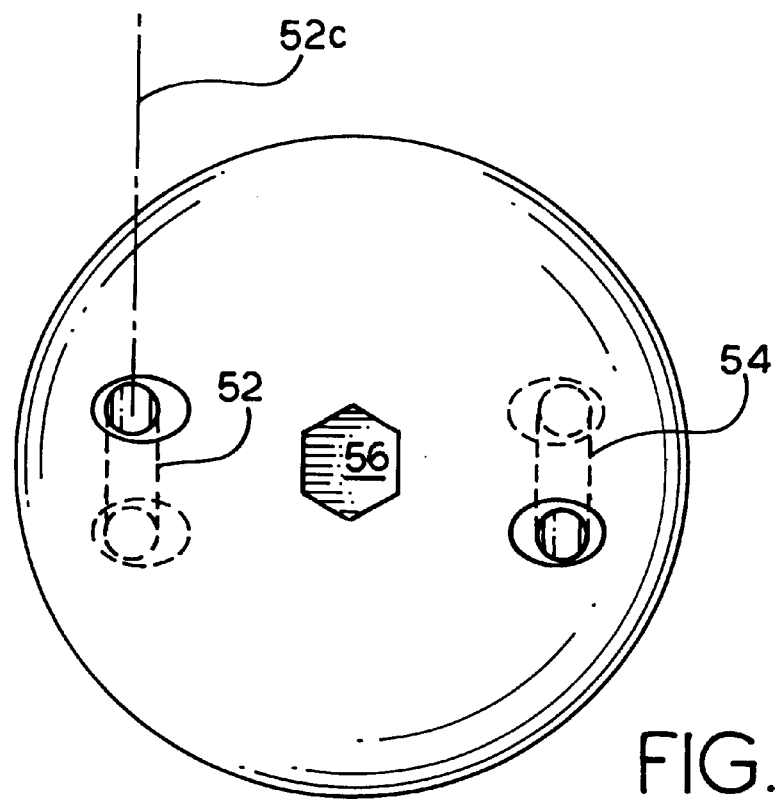
FIG. 4(a) is a top view of an alternate embodiment of a soft tissue securing anchor according to the present invention.
Figure 4B:
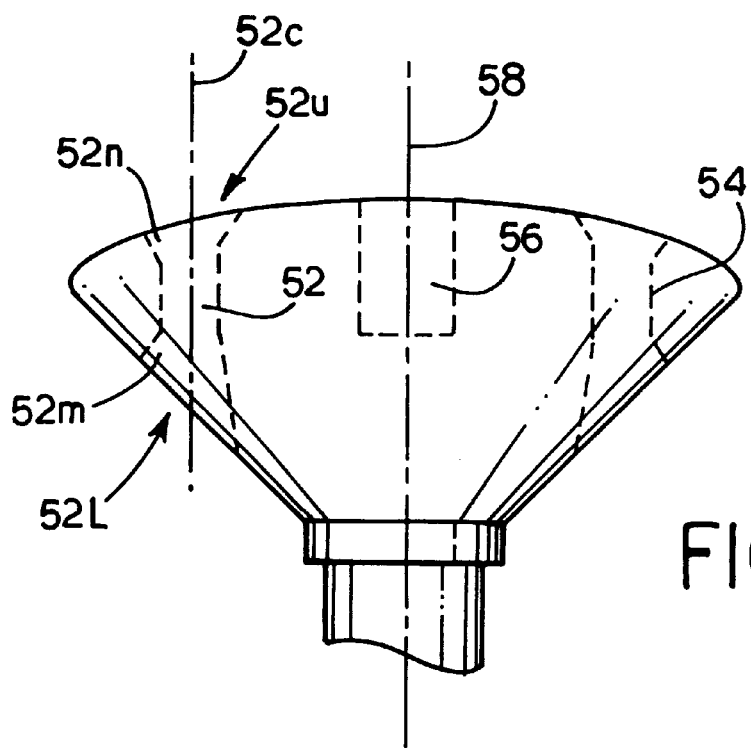
FIG. 4(b) is a side view of the soft tissue securing anchor of FIG. 4(a).

Referring now to FIGS. 4(a) and (b), an alternate embodiment of the present invention is shown in which anchor holes 52 and 54 are oriented skew to long axis 58. Each anchor hole has an upper aperture and a lower aperture. Anchor hole 52 includes upper aperture 52U and lower aperture 52L. Each aperture is chamfered. Upper aperture 52U includes aperture 52N. With anchor holes 52 and 54 oriented as shown in FIGS. 4(a) and (b), the angle formed between the anchor holes and a plane perpendicular to long axis 58 may be from 0° to 90°.

Figure 5A:
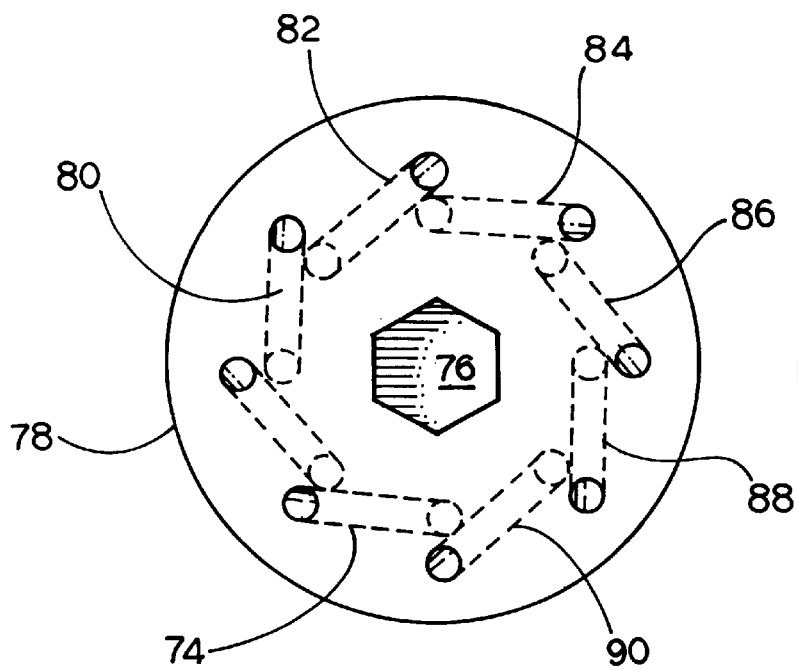
FIG. 5(a) is a top view of an alternate embodiment of a soft tissue securing anchor according to the present invention.
Figure 5B:
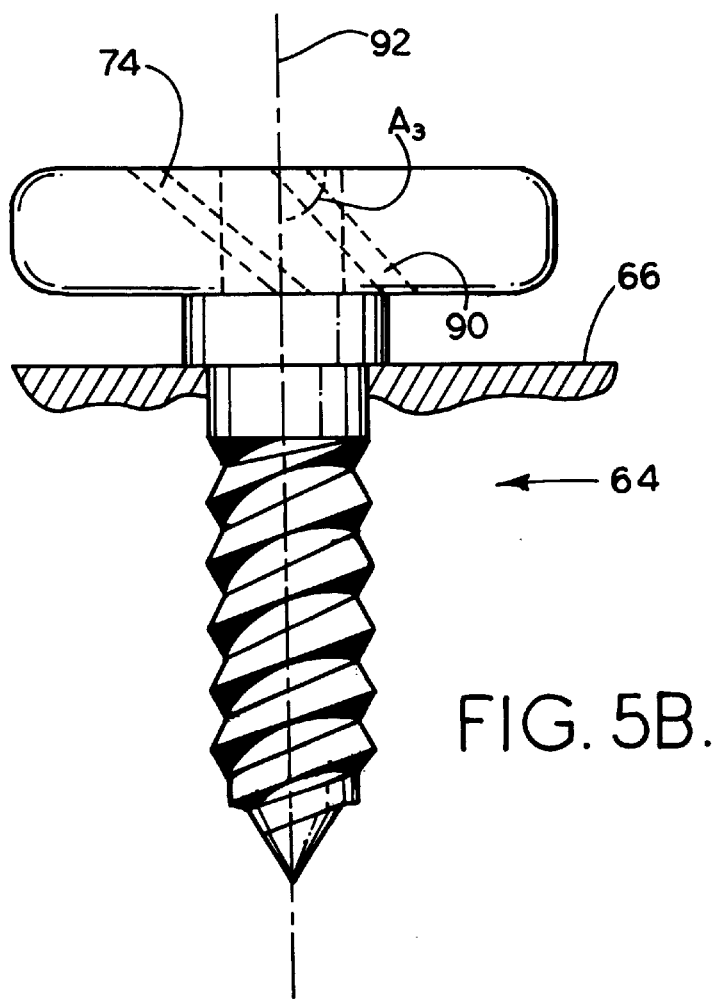
FIG. 5(b) is a side view of the soft tissue securing anchor of FIG. 5(a).

Referring now to FIGS. 5(a) and (b), an alternate embodiment of the present invention is shown in which lower surface 20 Anchor holes 74, 78, 80, 82, 84, 86, 88 and 90 are oriented generally parallel to drive socket 76. In FIG. 5(b) only anchor holes 74 and 90 are shown for clarity. With the anchor holes 74 and 90 oriented as shown in FIGS. 5(a) and (b), the angle formed between the anchor holes and a plane perpendicular to long axis 92 may be from 0° to 90°.

Figure 6A:
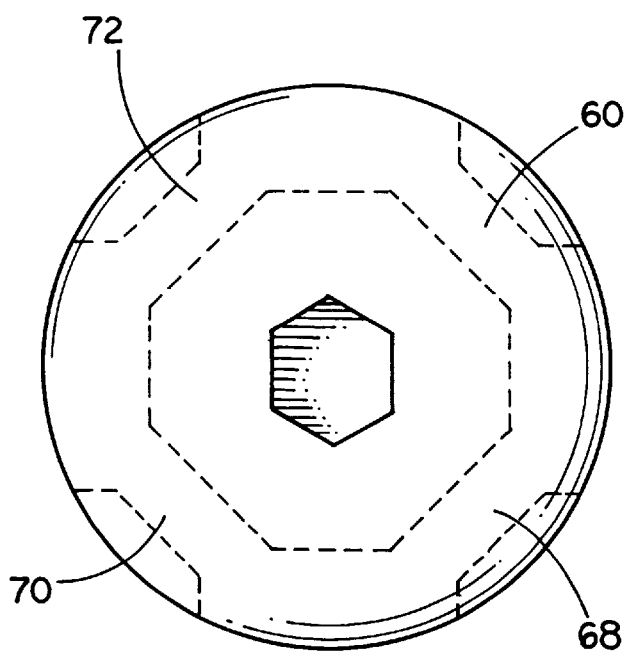
FIG. 6(a) is a top view of an alternate embodiment of a soft tissue securing anchor according to the present invention.
Figure 6B:
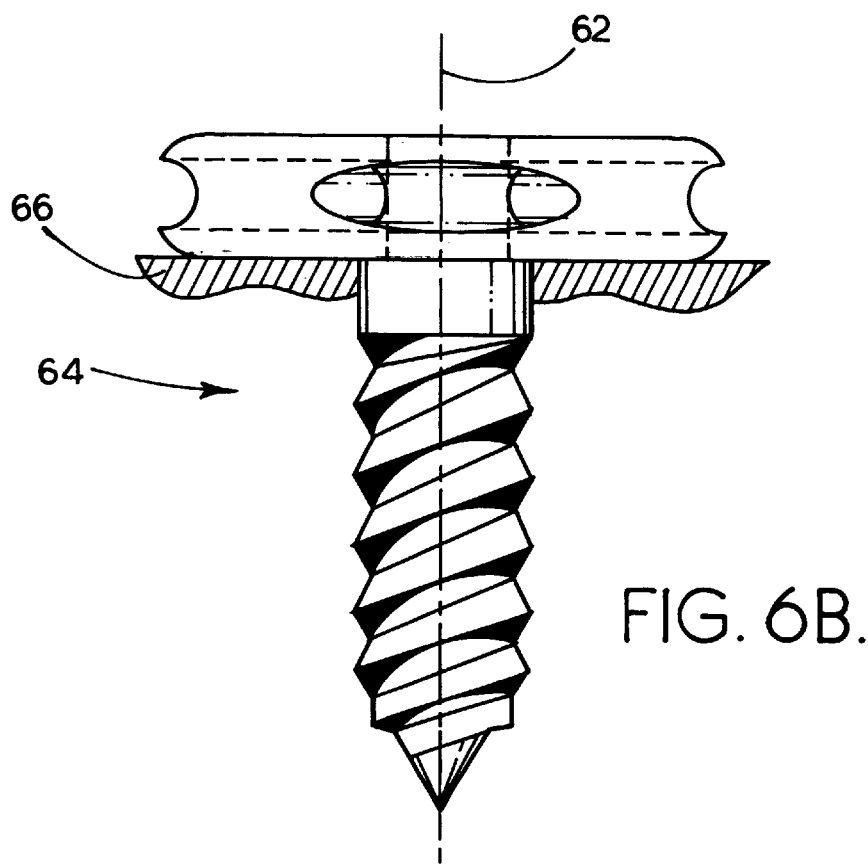
FIG. 6(b) is a side view of the soft tissue securing anchor of FIG. 6(a).

Referring now to FIGS. 6(a) and (b), anchor holes 60, 68, 70 and 72 form an angle of 0° with a plane perpendicular to long axis 62. The embodiment of the present invention shown in FIGS. 6(a) and (b) allows a surgeon to obtain an adequate angle of approximation to successfully secure one or more sutures to soft tissue anchor 64 by maintaining the surgical needle with the plane of its curve parallel to the plane of the surface of bone 66 as the surgical needle is passed through anchor hole 60, 68, 70 or 72 of soft tissue securing anchor 64. This embodiment of the present invention also presents a low profile above the surface of the bone in which it is secured.

Having now described the invention in accordance with the requirements of the patent statutes, those skilled in this art will understand how to make changes and modifications in the present invention to meet their specific requirements or conditions.

What is claimed is:

1. An anchor for securing soft tissue to bone or to soft tissue comprising:

an anchor body having a long axis and a head at a first end of the long axis adapted to accommodate a tool for securing or driving the anchor body into bone; and an anchor hole through the head having a chamfered opening and having a longitudinal axis that is oriented along a line through the center of the anchor hole to intersect an extension of the long axis beyond the head.

2. The anchor of claim 1 further comprising:

a shoulder displaced about the anchor body near the head to provide a visual and tactile reference for maintaining proper head height above the bone.

3. An anchor for securing soft tissue to bone or to soft tissue comprising:

an attachment means having a long axis and a head at a first end of the long axis;

means to accommodate a securing or drive tool; and an anchor hole through the head, the anchor hole having an upper aperture and a lower aperture wherein the upper aperture and lower aperture are chamfered, the anchor hole oriented to cause a line through the center of the anchor hole to intersect an extension of the long axis beyond the head.

4. The anchor of claim 3 wherein the chamfer extends from 5 to 50 percent of the total length of an anchor hole.

5. The anchor of claim 1 further comprising:

a plurality of anchor holes disposed about the circumference of the head.

6. The anchor of claim 1 wherein the anchor body comprises:

an inert material.

7. The anchor of claim 1 wherein the anchor body comprises:

plastic, stainless steel, titanium alloy or absorbable material or a combination thereof.

8. The anchor of claim 1 wherein the anchor body comprises:

a screw.

9. The anchor of claim 8 wherein the head further comprises:

a drive aperture on the head adapted to accept a tool for imparting torque to the anchor.

10. The anchor of claim 1 wherein the head is generally conical having a vertex, an upper surface and a lower surface, the vertex of the head attached to the anchor body anchor body.

11. The anchor of claim 10 wherein the angle between the lower surface and the long axis is between 90 and 150 degrees.

12. The anchor of claim 10 wherein the angle between the anchor holes and the long axis is between 0 and 75 degrees.

13. The anchor of claim 10 wherein the angle between the anchor holes and the long axis is between 35 and 50 degrees, and the chamfers are 45 degrees from a centerline through each anchor hole.

14. A surgical anchor for reapproximating soft tissue to bone or to soft tissue comprising:

a screw having a head, a shank and a threaded end, a shoulder between the head and the shank to provide a visual and tactile reference for proper head height above the bone;

the head including means to accommodate a securing or drive tool and a plurality of anchor holes radially displaced from a center of the head and disposed about a circumference of the head and extending through the head, each anchor hole having a chamfered end and having a long axis that defines an angle between 0 and 75 degrees with respect to the shank.

15. The anchor of claim 14 wherein the anchor comprises an inert material.

16. The anchor of claim 14 wherein the anchor comprises plastic, stainless steel, titanium alloy or absorbable material or a combination thereof.

17. The anchor of claim 14 wherein the anchor holes are skewed about the shank.

18. A surgical anchor for reapproximating soft tissue to bone or to soft tissue comprising:
    a screw having a head, a shank and a threaded end;
    a shoulder between the body and the shank to provide a visual and tactile reference for proper head height above the bone;
    means to accommodate a securing or drive tool; and
    a plurality of generally radial anchor holes disposed about the circumference of the head and extending through the head, each anchor hole describing an angle between 0 and 75 degrees from the shank to a line through the anchor hole, wherein the plurality of anchor holes further comprise apertures that are chamfered with a chamfer extending from 5 to 50 percent of the total length of an anchor hole.

19. The anchor of claim 14 wherein the head is an inverted cone having a generally flat upper surface and a sloping lower surface describing an angle between 90 and 150 degrees from the surface of the shank.

20. The anchor of claim 14 wherein the means to accommodate a securing or drive tool comprises a drive aperture on the head to accept a tool for imparting torque to the anchor.

21. An anchor body having a long axis;
    a head at a first end of the long axis to accommodate a tool for securing or driving the anchor body to bone; and
    an anchor hole through the head, the anchor hole having an upper aperture and a lower aperture, one of said upper and lower apertures including a chamfer, the anchor hole having a longitudinal axis that is oriented at an angle with respect to a long axis of the body.

22. The anchor of claim 21 further comprising:
    a shoulder displaced about the anchor body near the head to provide a visual and tactile reference for maintaining proper head height above the bone.

23. An anchor for securing soft tissue to bone or to soft tissue comprising:
    an attachment means having a long axis and a head at a first end of the long axis;
    means to accommodate a securing or drive tool; and
    an anchor hole through the head, the anchor hole having an upper aperture and a lower aperture wherein the upper aperture and lower aperture are chamfered, the anchor hole oriented to cause a line through the center of the anchor hole to be skew to the long axis.

24. The anchor of claim 23 wherein the chamfer extends from 5 to 50 percent of the total length of an anchor hole.

25. The anchor of claim 21 further comprising:
    a plurality of anchor holes disposed about the circumference of the head.

26. The anchor of claim 21 wherein the anchor holes are in a plane perpendicular to the long axis.

27. The anchor of claim 21 wherein the anchor body comprises:
    a screw.

28. The anchor of claim 27 wherein the head further comprises:
    a drive aperture on the head adapted to accept a tool for imparting torque to the anchor.

29. The anchor of claim 21 wherein the anchor body comprises:
    an inert material.

30. The anchor of claim 21 wherein the anchor body comprises:
    plastic, stainless steel, titanium alloy or absorbable material or a combination thereof.

31. The anchor of claim 21 wherein the head is generally conical having a vertex, an upper surface and a lower surface, the vertex of the head attached to the anchor body collinear with the long axis of the anchor body.

32. The anchor of claim 31 wherein the angle between the lower surface and the long axis is between 90 and 150 degrees.

33. The anchor of claim 31 wherein the angle between the anchor holes and the long axis is between 0 and 75 degrees.

34. The anchor of claim 31 wherein the angle between the anchor holes and the long axis is between 35 and 50 degrees, and the chamfers are 45 degrees from a centerline through each anchor hole.

35. The anchor of claim 1 wherein the upper aperture and lower aperture are chamfered.

36. The anchor of claim 35 wherein the chamfer extends from 5 to 50 percent of the total length of an anchor hole.

37. The anchor of claim 14 wherein the plurality of anchor holes further comprise apertures that are chamfered with a chamfer extending from 5 to 50 percent of the total length of an anchor hole.

38. The anchor of claim 21 wherein the upper aperture and lower aperture are chamfered.

39. The anchor of claim 38 wherein the chamfer extends from 5 to 50 percent of the total length of an anchor hole.

40. An anchor comprising:
    a one piece body having a long axis;
    a head at a first end of the body adapted to accommodate a securing or drive tool; and
    an elongate anchor bore through the head, a centerline of the elongate anchor bore aligned with respect to the body to be oriented at an angle with respect to the long axis of the body so as to intersect the long axis at a location spaced from the body, and a chamfer in said head adjacent to said bore.

41. The anchor of claim 40 further comprising:
    a shoulder displaced about the one piece body near the head to provide a visual and tactile reference for maintaining proper head height above the bone.

42. The anchor of claim 40 wherein the upper aperture and lower aperture are chamfered.

43. The anchor of claim 42 wherein the chamfer extends from 5 to 50 percent of the total length of an elongate anchor bore.

44. The anchor of claim 40 further comprising:
    a plurality of elongate anchor bores disposed about the circumference of the head.

45. The anchor of claim 40 wherein the one piece body comprises:
    an inert material.

46. The anchor of claim 40 wherein the one piece body comprises:
    a one piece attachment of plastic, stainless steel, titanium alloy or absorbable material or a combination thereof.

47. The anchor of claim 40 wherein the one piece body comprises:
    a screw.

48. The anchor of claim 47 wherein the head further comprises:
a drive aperture adapted to accept a tool for imparting torque to the anchor.

49. The anchor of claim 40 wherein the head is generally conical having a vertex, an upper surface and a lower surface, the vertex attached to the body collinear with the long axis of the body.

50. The anchor of claim 49 wherein an angle between the lower surface and the long axis is between 90 and 150 degrees.

51. The anchor of claim 49 wherein an angle between the elongate anchor bores and the long axis is between 0 and 75 degrees.

52. The anchor of claim 49 wherein an angle between the elongate anchor bores and the long axis is between 35 and 50 degrees, and the chamfers are 45 degrees from a centerline through each elongate anchor bore.

53. The anchor of claim 40 wherein the chamfer extends from 5 to 50 percent of the total length of an elongate anchor bore.

54. The anchor of claim 40 further comprising:
a plurality of elongate anchor bores disposed about a circumference of the head.

55. The anchor of claim 54 wherein the angle between the centerline of each of the plurality of elongate anchor bores and a line parallel to the long axis is between 0 and 75 degrees.

56. The anchor of claim 54 wherein the angle between the centerline of each of the plurality of elongate anchor bores and a line parallel to the long axis is between 35 and 50 degrees, and the chamfers are 45 degrees from a centerline through each elongate anchor bore.

57. An anchor comprising:
an anchor body having a stop thereon which is located to engage a patient's bone when the anchor body is inserted into the bone preset depth; and
a channel defined through the anchor body, the channel having a chamfer on one end thereof and being located to be above the bone when the anchor body is inserted into the bone at the preset depth of anchor body insertion.

58. The anchor of claim 57 wherein the anchor body further comprises:
a long axis; and
a centerline of the channel is oriented to intersect an extension of the long axis beyond the anchor body.

59. The anchor of claim 58 wherein a centerline of the channel is oriented skew to the long axis.

60. The anchor of claim 57 wherein the channel includes a chamfered second aperture.

61. The anchor of claim 58 wherein at least one of said chamfers extends from 5 to 50 percent of the total length of the channel.

62. The anchor of claim 58 wherein the anchor body further comprises:
a head; and
a plurality of channels disposed about a circumference of the head.

63. The anchor of claim 57 wherein the anchor body comprises:
an inert material.

64. The anchor of claim 57 wherein the anchor body comprises:
plastic, stainless steel, titanium alloy or absorbable material or a combination thereof.

65. The anchor of claim 57 wherein the anchor body comprises:
a screw.

66. The anchor of claim 62 wherein the head further comprises:
means adapted for imparting torque to the anchor.

67. The anchor of claim 62 wherein the head is generally conical having a vertex, an upper surface and a lower surface, the vertex attached to the anchor body collinear with the long axis.

68. The anchor of claim 67 wherein an angle between the lower surface and the anchor body is between 90 and 150 degrees.

69. The anchor of claim 67 wherein an angle between the anchor channels and the long axis is between 0 and 75 degrees.

70. The anchor of claim 67 wherein an angle between the anchor channels and the long axis is between 35 and 50 degrees, and the chamfers are 45 degrees from a centerline through each anchor channel.

71. The anchor of claim 69 wherein an angle between a centerline of each of the plurality of anchor channels and a line parallel to the long axis is between 0 and 75 degrees.

72. The anchor of claim 70 wherein the angle between a centerline of each of the plurality of anchor channels and a line parallel to the long axis is between 35 and 50 degrees, and the chamfers are 45 degrees from a centerline through each anchor channel.

73. An anchor comprising:
an anchor body having a long axis;
a head at a first end of the anchor body adapted to accommodate a tool for securing or driving the anchor body into bone; and
a passage through the head, said passage having a longitudinal axis that is oriented to intersect the long axis of the body at a location outside of the anchor body and having a chamfer on one end thereof.

74. An anchor comprising:
an anchor body having a long axis;
a head at a first end of the anchor body adapted to accommodate a tool for securing or driving the anchor body into bone; and
a passage through the head, said passage having a longitudinal axis that is oriented at an oblique angle with respect to the long axis of the anchor body and having a chamfer on one end thereof.

75. An anchor comprising:
an anchor body having a long axis;
a head at a first end of the anchor body adapted to accommodate a tool for securing or driving the anchor body into bone; and
a plurality of passages through the head, each passage including a chamfered end and a longitudinal axis that is oriented to intersect the long axis at a location spaced from the anchor body.

76. An anchor comprising:
an anchor body having a long axis;
a head at a first end of the anchor body adapted to accommodate a tool for securing or driving the anchor body into bone; and
a plurality of passages through the head, each passage having a longitudinal axis that is oriented at an oblique angle with respect to the long axis of the anchor body and at least one passage having a chamfer on one end thereof.

* * * * *